(12) United States Patent
Slaughter et al.

(10) Patent No.: US 7,854,741 B2
(45) Date of Patent: *Dec. 21, 2010

(54) PIGMENTARY GLAUCOMA IRIS SCRAPING TREATMENT OF THE IRIS

(76) Inventors: Eva M. T. Slaughter, 71 Wilkes Ave., Buffalo, NY (US) 14215-3511; Tawan S. Slaughter, 71 Wilkes Ave., Buffalo, NY (US) 14215-3511

(*) Notice: Subject to any disclaimer, the term of this patent is extended or adjusted under 35 U.S.C. 154(b) by 751 days.

This patent is subject to a terminal disclaimer.

(21) Appl. No.: 11/825,502

(22) Filed: Jul. 6, 2007

(65) Prior Publication Data

US 2009/0012550 A1 Jan. 8, 2009

(51) Int. Cl.
*A61B 17/24* (2006.01)
(52) U.S. Cl. ..................................... 606/161
(58) Field of Classification Search ............... 606/161, 606/162, 166, 167, 169; 604/22
See application file for complete search history.

(56) References Cited

U.S. PATENT DOCUMENTS

| | | | | |
|---|---|---|---|---|
| 5,098,438 | A | * | 3/1992 | Siepser ....................... 606/107 |
| 6,428,501 | B1 | * | 8/2002 | Reynard ....................... 604/27 |
| 2007/0161981 | A1 | * | 7/2007 | Sanders et al. ................ 606/41 |

* cited by examiner

*Primary Examiner*—Anhtuan T Nguyen
*Assistant Examiner*—Sarah A Simpson
(74) *Attorney, Agent, or Firm*—Eva M. T. Slaughter; Tawan S. T. Slaughter; Javon Z. T. Slaughter

(57) ABSTRACT

An iris scraping surgical method treats pigmentary glaucoma in which the pigment attaches to the underside of the iris. An incision is made in the sclera. The iris is lifted and pigment and/or cellular debris is scraped with a scalpel from the bottom layer (pigment epithelium) of the iris. The iris lifted up from the lens to remove the build up of escaping pigment on that layer to let the fluid flow out at a normal rate to drain out of the trabecular meshwork and then the iris is lowered and the incision in the sclera is closed.

2 Claims, 4 Drawing Sheets

PIGMENTARY GLAUCOMA IRIS SCRAPING TREATMENT OF THE IRIS

CROSS-REFERENCE TO RELATED APPLICATIONS

Not Applicable.

STATEMENT REGARDING FEDERALLY SPONSORED RESEARCH OR DEVELOPMENT

Not Applicable.

THE NAMES OF THE PARTIES TO A JOINT RESEARCH OR DEVELOPMENT

Not Applicable.

BACKGROUND OF THE INVENTION

1. Field of the Invention

The present invention relates to glaucoma treatments and particularly to a surgical iris scraping treatment for pigmentary glaucoma wherein the pigment debris is on the bottom layer of the iris and wherein an incision is made in the sclera, the iris is lifted and pigment and/or cellular debris is scraped preferably with a scalpel from the bottom layer (pigment epithelium) of the iris; the iris lifted up from the lens to remove the build up of escaping pigment on that layer to let the fluid flow out at a normal rate to drain out of the trabecular meshwork and then the incision in the sclera is closed.

2. Description of Related Art Including Information Disclosed Under 37 CFR 1.97 and 1.98

Worldwide, glaucoma is the leading cause of irreversible blindness. In fact, as many as six million individuals are blind in both eyes from this disease. In the United States alone, according to one estimate, over three million people have glaucoma. As many as half of the individuals with glaucoma, however, may not know that they have the disease. The reason they are unaware is that glaucoma initially causes no symptoms, and the loss of vision on the side (periphery) is hardly noticeable.

Glaucoma is usually, but not always, associated with elevated pressure in the eye (intraocular pressure). This pressure leads to damage to the eye (optic) nerve. Actually, glaucoma is now considered a disease of the optic nerve (optic neuropathy) that causes a loss of vision, usually in both eyes (bilateral). This loss often begins with a subtle decrease in side (peripheral field) vision. If the glaucoma is not diagnosed and treated, it may progress to loss of central vision and blindness.

Pigmentary glaucoma is a rare form of glaucoma wherein pigment from the iris pigment epithelium is shed thereby releasing pigment particles into the aqueous humor which clog the trabecular meshwork, preventing the drainage of aqueous humor from the anterior chamber. In certain circumstances, the granules of pigment get stuck on a portion of the bottom layer of the iris and partially block the flow of fluid between the iris and the lens to cause a pressure build up in the eye. Pigmentary glaucoma is a type of secondary glaucoma that is more common in younger men. In this condition, for reasons not yet understood, granules of pigment detach from the iris, which is the colored part of the eye. These granules then may block the trabecular meshwork, which, as noted above, is the drainage system of the eye or may stick to the bottom layer of the iris to block the flow of fluid between the iris and the lens. Finally, the blocked drainage system leads to elevated intraocular pressure, which results in damage to the optic nerve.

Apparently the cause of the pressure build-up in the eye which is a build-up of pigment debris and dead cell tissues on the back of the iris which covers the lens of the eye. When the pigment debris and dead cell tissue harden to block the flow of fluid, it causes the level of the pressure in the eye to rise, even to dangerous levels. These levels of high pressure build up in the eye, depend upon the amount of pigment debris and dead cell tissue present.

Iris color is a highly complex phenomenon consisting of the combined effects of texture, pigmentation, fibrous tissue and blood vessels within the iris stroma, which together make up an individual's epigenetic constitution. A person's "eye color" is actually the color of one's iris, the cornea being transparent and the white sclera entirely outside the area of interest. It is a common misconception that the iris color is entirely due to its melanin pigment; this varies only from brown to black.

Melanin is yellowish-brown to dark brown in the stromal pigment cells, and black in the iris pigment epithelium, which lies in a thin but very opaque layer across the back of the iris. Most human irises also show a condensation of the brownish stromal melanin in the thin anterior border layer, which by its position has an overt influence on the overall color. The degree of dispersion of the melanin, which is in subcellular bundles called melanosomes, has some influence on the observed color, but melanosomes in the iris of man and other vertebrates are not mobile, and the degree of pigment dispersion cannot be reversed. Abnormal clumping of melanosomes does occur in disease and may lead to irreversible changes in iris color (see heterochromia, below). Colors other than brown or black are due to selective reflection and absorption from the other stromal components. Sometimes lipofuscin, a yellow "wear and tear" pigment also enters into the visible eye color, especially in aged or diseased green eyes (but not in healthy green human eyes).

While a number of methods exist for treating pigmentary glaucoma due to the clogging of the trabecular meshwork by pigment debris from the iris, the prior art is lacking in treatments for the build-up of pigment debris on the bottom layer of the iris to block the flow of fluid between the iris and the lens.

U.S. Patent Application #20060241580, published Oct. 26, 2006 by Mittelstein, claims a device and methods useable for treatment of glaucoma, including pigmentary glaucoma, and other surgical procedures. A device and method are provided for cutting or ablating tissue in a human or veterinary patient includes an elongate probe having a distal end, a tissue cutting or ablating apparatus located adjacent within the distal end, and a tissue protector extending from the distal end. The protector generally has a first side and a second side and the tissue cutting or ablating apparatus is located adjacent to the first side thereof. The distal end is structured to be advanceable into tissue or otherwise placed and positioned within the patient's body such that tissue adjacent to the first side of the protector is cut away or ablated by the tissue cutting or ablation apparatus while tissue that is adjacent to the second side of the protector is not substantially damaged by the tissue cutting or ablating apparatus.

U.S. Pat. No. 5,549,596, issued Aug. 27, 1996 to Latina, provides a selective laser method of targeting pigmented ocular cells which involves selectively damaging pigmented cells in an intraocular area by irradiating the area with laser radiation of radiant exposure between about 0.01 and about 5 Joules/cm.sup.2, while sparing non-pigmented cells and collagenous structures within the irradiated area. The method is useful for the treatment of glaucoma, intraocular melanoma, and macular edema.

U.S. Pat. No. 6,989,007, issued Jan. 24, 2006 to Shadduck, shows a device and system for non-invasive treatment of a patient's trabecular meshwork to treat primary open-angle glaucoma or pigmentary glaucoma. The system and technique applies energy directly to media within clogged spaces in a patient's trabecular meshwork to increase aqueous outflow facility by (i) localization of microimplantable bodies carrying a selected exogenous chromophore, such as particles with a gold surface, in deeper regions of the trabecular meshwork, and (ii) irradiation of the microimplantables with a selected coherent wavelength having a power level and pulse duration that is strongly absorbed by the surfaces of the microimplantables.

U.S. Pat. No. 6,682,523, issued Jan. 27, 2004 to Shadduck, claims a system for non-invasive treatment of a patient's trabecular meshwork to treat primary open-angle glaucoma, exfoliation glaucoma and pigmentary glaucoma wherein the meshwork can be clogged with cellular debris and other accumulations. The system and technique applies energy directly to media within clogged spaces in a patient's trabecular meshwork to increase aqueous outflow facility by (i) localization of microimplantable bodies carrying a selected exogenous chromophore in deeper regions of the trabecular meshwork and (ii) irradiation of the microimplantables with a selected coherent wavelength having a power level and pulse duration that is strongly absorbed by the exogenous chromophore. The chromophores are preferably carried in uniform nanocrystalline particles having an average diameter ranging from about 0.5 nm to 20 nm. Thermoelastic expansion of the nanoparticles can propagate .+-.10 atm bipolar stress waves in the surrounding fluid media thereby causing microcavitation thereby delivering mechanical energy to ablate debris and accumulations in the meshwork without causing thermal damage to the trabecular meshwork sheets.

U.S. Pat. No. 6,319,274, issued Nov. 20, 2001 to Shadduck, describes an apparatus and technique for transscleral light-mediated biostimulation of the trabecular plates of a patient's eye in a treatment for ocular hypertension or glaucoma, including pigmentary glaucoma. The apparatus includes; (i) a working end geometry for contacting the anterior surface of the sclera and cornea to insure that a laser emission reaches the trabecular meshwork from a particular location on the anterior surface of the sclera, (ii) a laser energy source providing a wavelength appropriate for absorption beneath the anterior scleral surface to the depth of the trabecular plates, and (iii) a dosimetry control system for controlling the exposure of the laser emission at the particular spatial locations. The device uses a light energy source that emits wavelengths in the near-infrared portion of the spectrum, preferably in the range of about 1.30 .mu.m to 1.40 .mu.m or from about 1.55 mu.m to 1.85 mu.m. The depth of absorption of such wavelength ranges will extend through most, if not all, of the thickness of the sclera (750 .mu.m to 950 .mu.m). In accordance with a proposed method of trabecular biostimulation, the targeted region is elevated in temperature to a range between about 40.degree. C. to 55.degree. C. for a period of time ranging from about 1 second to 120 seconds or more.

U.S. Pat. No. 4,391,275, issued Jul. 5, 1983 to Fankhauser, discloses a method for the surgical treatment of the eye by perforation, by laser radiation, of a tissue or inner wall of the eyeball having a resistance to the free circulation of the aqueous humour. A laser radiation burst comprising at least one pulse of duration d comprised between 10 and 60 ns and of radiated energy comprised between 30 and 300 millijoules is produced and focused at a determined distance inside the wall. The radiation is focused according to a solid angle OMEGA. determining a density of radiated energy causing ionization of the propagation medium. A shock wave is also produced due to this ionization close to the mean direction of propagation of the radiated, thereby allowing the tissue or inner wall to be perforated.

U.S. Pat. No. 6,220,247, issued Apr. 24, 2001 to Maldonado Bas, indicates a method of performing trabeculodissection to treat glaucoma using an excimer or galvanometric scanning laser delivery system. A scleral flap is cut to expose the treatment area of the trabecular meshwork. The arc of the treatment area is made as wide as the trabecular meshwork limited by the circumference of the limbal area around the patient's eye. A laser, preferably of the excimer type, is used to treat small test areas in successive discrete zones along the arc of the treatment area in the bed of the scleral flap to determine the precise depth of ablation required over the entirety of each zone to promote filtration without penetration of the treatment zone. The laser then treats discrete zones over the length of the arc to remove in scan layers so as to process discrete ablated zones of minimal residual thickness. The treatment of successive zones allows ablation along the length of the treatment arc without interference from actively draining aqueous. After ablation of the various successive zones, the scleral flap is closed and, if necessary, sutured.

U.S. Patent Application #20050288745, published Dec. 29, 2005 by Andersen, describes a method and device for optical ophthalmic therapy, which includes treatment for different forms of glaucoma, including pigmentary glaucoma. An optical scanning system and method are provided for performing therapy on trabecular meshwork of a patient's eye, including a light source for producing alignment and therapeutic light, a scanning device for deflecting the alignment and therapeutic light to produce an alignment therapeutic patterns of the alignment and therapeutic light, and an ophthalmic lens assembly for placement over a patient's eye that includes a reflective optical element for reflecting the light patterns onto the trabecular meshwork of the patient's eye. The reflective optical element can be a continuous annular mirror (e.g. smooth or with multiple facets) to image the entire trabecular meshwork, or a reflective optical element that moves in coordination with the deflection of the beam. Visualization of the alignment and therapeutic patterns of light on the eye can be implemented by reflection thereof off a visualization mirror that transmits a portion of light emanating from the trabecular meshwork.

U.S. Patent Application #20030109907, published Jun. 12, 2003 by Shadduck, discloses devices and techniques for light-mediated stimulation of trabecular meshwork in glaucoma therapy, including pigmentary glaucoma therapy. An apparatus and technique are provided for transscleral light-mediated biostimulation of the trabecular plates of a patient's eye in a treatment for glaucoma or ocular hypertension. The apparatus includes; (i) a working end geometry for contacting the anterior surface of the sclera and cornea to insure that a laser emission reaches the trabecular meshwork from a particular location on the anterior surface of the sclera, (ii) a laser energy source providing a wavelength appropriate for absorption beneath the anterior scleral surface to the depth of the trabecular plates, and (iii) a dosimetry control system for controlling the exposure of the laser emission at the particular spatial locations. The device uses a light energy source that emits wavelengths in the near-infrared portion of the spectrum, preferably in the range of about 1.30 mu.m to 1.40 mu.m or from about 1.55 .mu.m to 1.85 .mu.m. The depth of absorption of such wavelength ranges will extend through most, if not all, of the thickness of the sclera (750 .mu.m to 950 .mu.m). In accordance with a proposed method of trabecular biostimulation, the targeted region is elevated in temperature to a range between about 40.degree. C. to 55.degree. C. for a period of time ranging from about 1 second to 120 seconds or more.

U.S. Pat. No. 6,306,127, issued Oct. 23, 2001 to Homer, is for a method for altering iris pigmentation in a human, thereby altering perceived iris color of a first iris from a first iris color to a second iris color. The method comprises pre-selecting one or more than one laser capable of generating one or more than one laser beam which will selectively remove iris pigment of a first pre-selected pigment color from the first iris, and applying the one or more than one laser beam to the first iris of a first iris color to remove iris pigment of the first pre-selected pigment color.

What is needed is a method for removing the build-up of pigment debris on the bottom layer of the iris which blocks the flow of fluid between the iris and the lens.

BRIEF SUMMARY OF THE INVENTION

An object of the present invention is to provide a method for removing the build-up of pigment debris on the bottom layer of the iris which blocks the flow of fluid between the iris and the lens.

In brief, the present invention provides an iris scraping procedure to cure a type of pigmentary glaucoma where the pigment build-up on the bottom layer of the iris causes a blockage of fluid drainage. The method comprises partially cutting the film layer (sclera) over the iris and lift one edge of the iris and use a scalpel or a debridement tool to carefully scrape the pigment debris and dead cell tissue from the film layer on the underside of the iris without disturbing the film, and lower the iris back down and re-attach the iris by suturing or other means.

The surgical procedure method of the present invention cleans the back of the iris to restore vision and relieve the pressure.

An advantage of the present invention is that it relieves the pressure of the fluid build-up by removing the blockage to relieve the pain of the patient and also provide brighter and clearer vision.

BRIEF DESCRIPTION OF THE SEVERAL VIEWS OF THE DRAWINGS

These and other details of my invention will be described in connection with the accompanying drawings, which are furnished only by way of illustration and not in limitation of the invention, and in which drawings.

DETAILED DESCRIPTION OF THE INVENTION

Figure 1:
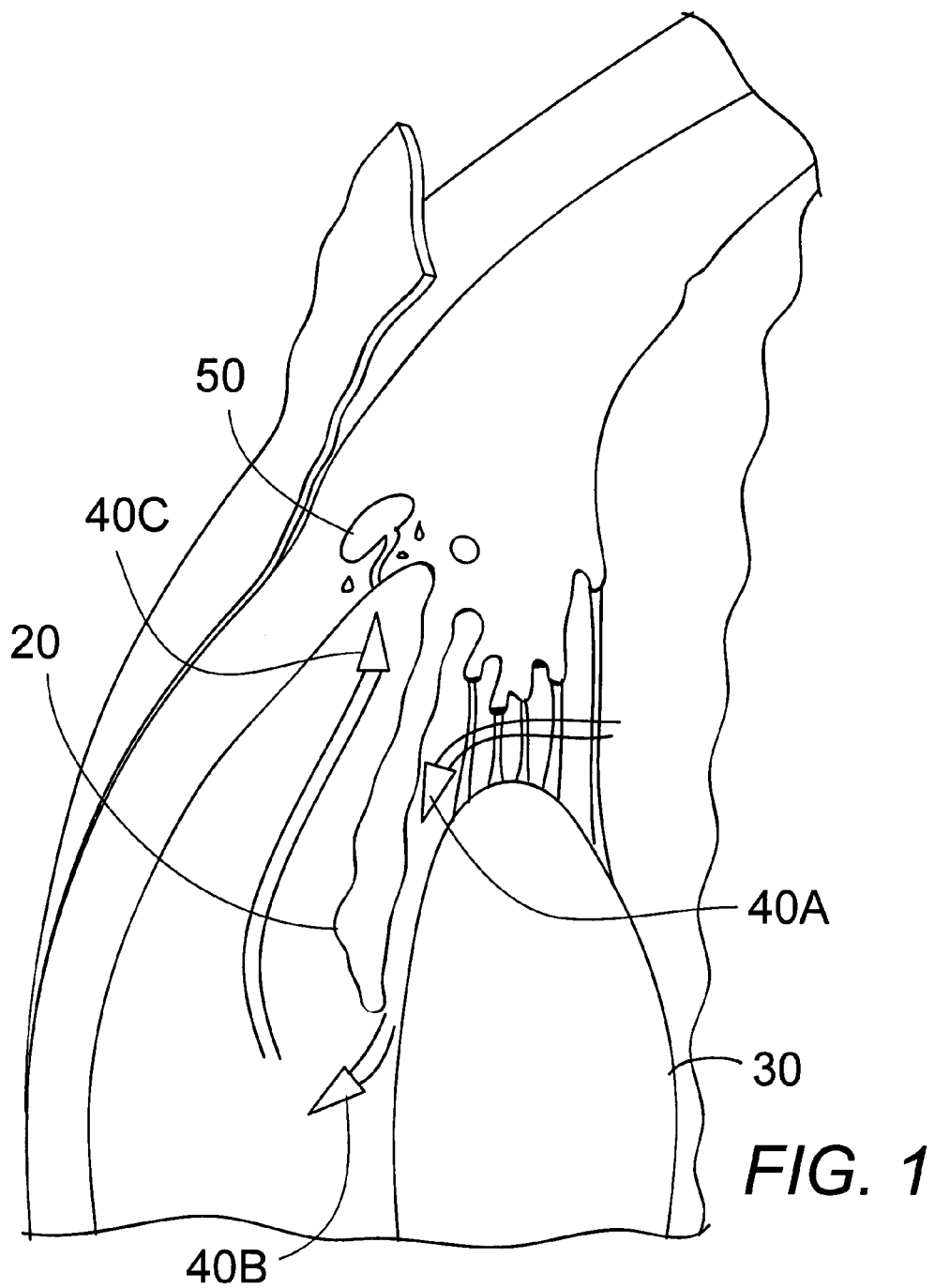
FIG. 1 is a partial cross-sectional view taken through the eye showing a portion of the iris and a portion of the lens with a clear passage of fluid between the iris and the lens.
Figure 2:
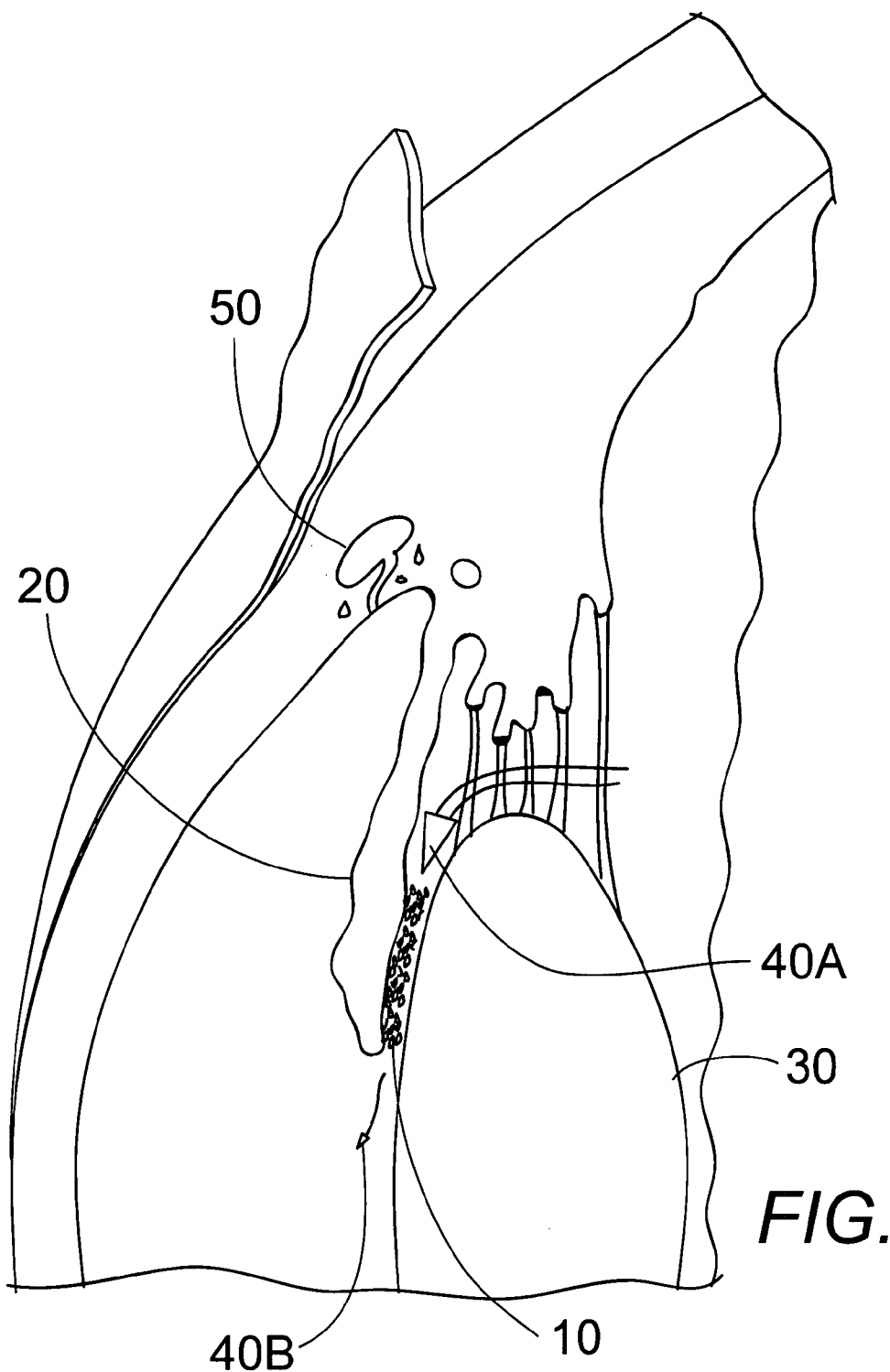
FIG. 2 is a partial cross-sectional view taken through the eye showing a portion of the iris and a portion of the lens with a build-up of pigment debris on the bottom of the iris blocking the flow of fluid between the iris and the lens.
Figure 3:
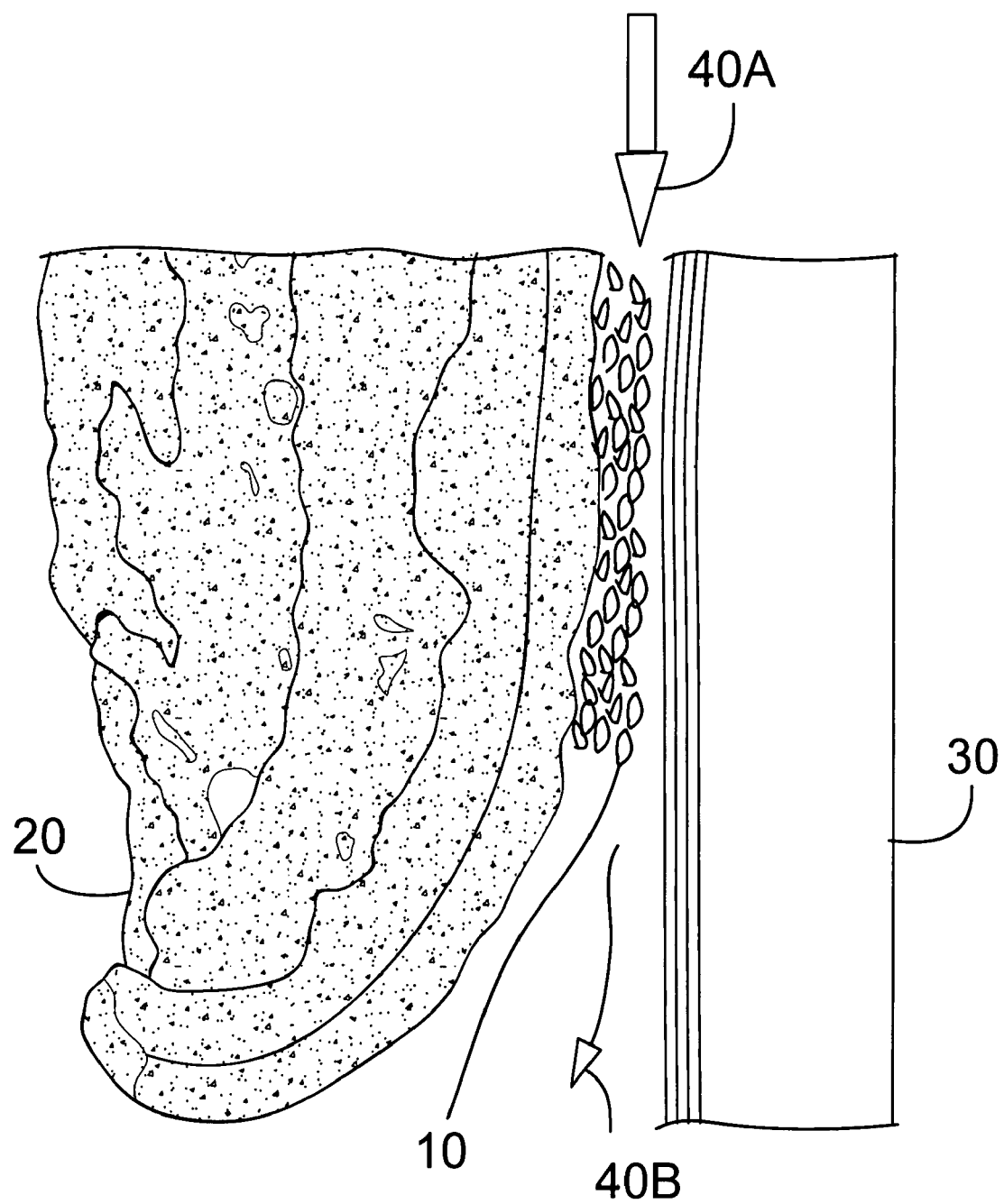
FIG. 3 is an enlarged partial cross-sectional view of FIG. 2 showing the build-up of pigment debris on the bottom of the iris blocking the flow of fluid between the iris and the lens.
Figure 4:
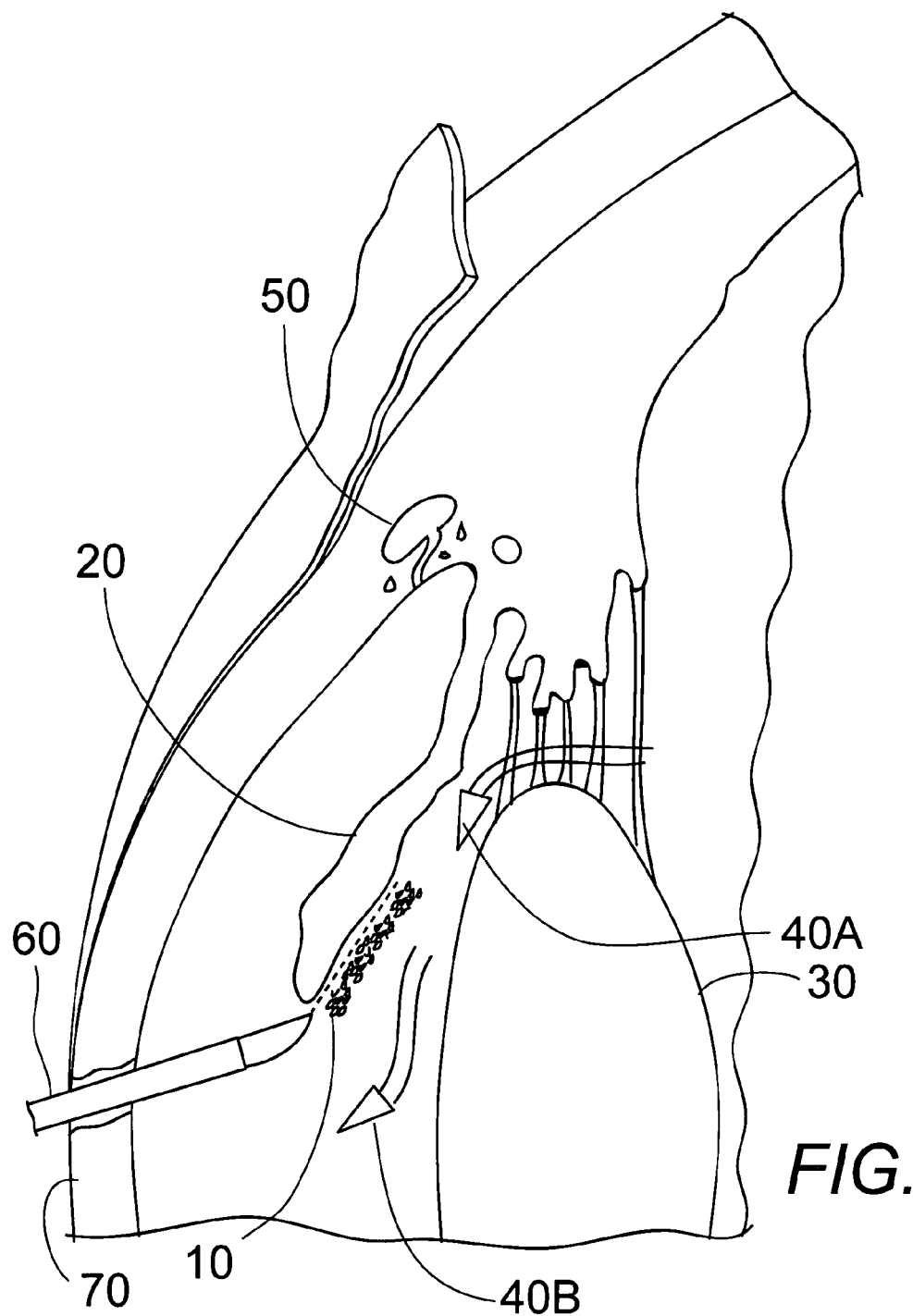
FIG. 4 is a partial cross-sectional view taken through the eye showing a portion of the iris and a portion of the lens with the iris lifted and an incision in the schlera and a curved blade surgical instrument, which is preferably a scalpel, through the incision removing a build-up of pigment debris on the bottom of the iris to free the flow of fluid between the iris and the lens.

In FIGS. 1-4, an iris scraping surgical method treats pigmentary glaucoma in which the pigment 10 attaches to the underside of the iris 20. In FIG. 4, an incision 71 is made in the sclera 70. The iris 20 is lifted and pigment and/or cellular debris 10 is scraped with a curved blade surgical tool, which is preferably a scalpel, from the bottom layer (pigment epithelium) of the iris 20. The iris 20 is lifted up from the lens 30 to remove the build up of escaping pigment 10 on that layer to let the fluid flow out at a normal rate of fluid flow 40B to drain out of the trabecular meshwork 50 and then the iris 20 is lowered and the incision 71 in the sclera 70 is closed.

The iris scraping surgical treatment method of the present invention for pigmentary glaucoma wherein pigment debris builds up on a bottom layer of an iris 20 to block fluid flow 40A to 40B between the iris 20 and the lens 30 of the eye, the method comprising:

a first step of making an incision 71 in the sclera 70;

a second step of lifting the iris 20 from the lens 30;

a third step of scraping pigment and cellular debris 10 from the bottom layer (pigment epithelium) of the iris 20 using a small pointed curved blade surgical instrument 60, which is preferably a scalpel, to remove the build up of escaping pigment on the bottom layer to let the fluid flow out at a normal rate to drain out of the trabecular meshwork 50 leaving the bottom layer of the iris intact; and a fourth step of closing the incision 71 in the sclera 70.

CAUTION: DO NOT PUNCTURE, DAMAGE, DESTROY, OR REMOVE THE EXISTING FILM THAT IS PERMANENTLY ATTACHED TO THE IRIS.

NOTE: ONLY 'ALL' DEBRIS AND DEAD CELL TISSUES CAN BE REMOVED.

It is understood that the preceding description is given merely by way of illustration and not in limitation of the invention and that various modifications may be made thereto without departing from the spirit of the invention as claimed.

What is claimed is:

1. An iris scraping surgical treatment method for pigmentary glaucoma wherein escaping pigment debris and cellular debris builds up on a bottom layer of an iris to block fluid flow between the iris and the lens of the eye, the method comprising:

a first step of making an incision in the sclera to access an iris of an eye of a patient having pigmentary glaucoma wherein the eye has a build up of escaping pigment debris and cellular debris accumulated on a bottom layer of the pigment epithelium of the iris blocking a flow of eye fluid normally flowing from an interior of the eye out between the iris and the lens to a drainage area of the trabecular epithelium;

a second step of lifting the iris from the lens to access the bottom layer of the pigment epithelium of the iris by moving the iris away from the lens a sufficient distance to access the bottom layer of the pigment epithelium for scraping only with a surgical instrument without cutting, puncturing, damaging or removing the iris;

a third step of scraping the pigment debris and cellular debris from the bottom layer of the pigment epithelium of the iris without damaging or removing the bottom layer of the pigment epithelium of the iris using a small pointed curved blade surgical instrument to remove the build up of the pigment debris and cellular debris from the bottom layer of the pigment epithelium leaving the bottom layer of the pigment epithelium unharmed and free from the pigment debris and cellular debris;

a fourth step of releasing the scraped iris so that the bottom layer of the pigment epithelium, free of the pigment debris and cellular debris, rests on the lens of the eye to let the fluid flow out at a normal rate to drain out of the back of the eye to flow between the bottom layer of the pigment epithelium of the iris and the lens of the eye out to the trabecular meshwork drainage area; and a fifth step of closing the incision in the sclera.

2. The method of claim 1 wherein the third step comprises using a scalpel as the small pointed curved blade surgical instrument.

* * * * *